US00PP16553P2

(12) United States Plant Patent
Utecht

(10) Patent No.: US PP16,553 P2
(45) Date of Patent: May 16, 2006

(54) *GERANIUM* PLANT NAMED 'GRAFIRE'

(50) Latin Name: *Pelargonium zonale*
Varietal Denomination: Grafire

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 55 days.

(21) Appl. No.: 10/998,664

(22) Filed: Nov. 30, 2004

(51) Int. Cl.
*A01H 5/00* (2006.01)

(52) U.S. Cl. ..... Plt./330
(58) Field of Classification Search ..... Plt./330, Plt./327, 328
See application file for complete search history.

(56) References Cited

PUBLICATIONS

German PBR Application No. PEL 1903 filed Jun. 4, 2003 and withdrawn Oct. 5, 2004 (Copy of German Gazettes dated 1) Jul. 15, 2003—Listing Assigned Application for Protection No. (2 pgs), 2) May 15, 2004—Publishing Proposed Variety Denomination (2 pgs), and 3) Nov. 15, 2004—Listing Withdrawal of Application for Protection (2 pgs)).

Canadian PBR Application No. 03–3902 filed Nov. 21, 2003 (Copy of Canadian Plant Varieties Journal dated Jan., 2004 Listing Assigned Application No. (2 pgs).

Community Plant Variety Office (CPVO) No. 2004/1254 filed Jul. 5, 2004 (Copy of Official Gazette of the CPVO dated Oct. 15, 2004 Listing Assigned Application No. and Variety Denomination (3 pgs).

Fischer 2005 catalogue offering 'Grafire' (with shipment of plant material available starting Dec., 2004) (3 pgs).

*Primary Examiner*—Kent Bell
(74) *Attorney, Agent, or Firm*—Foley & Lardner LLP

(57) ABSTRACT

A new and distinct cultivar of *geranium* plant named 'Grafire' particularly characterized by the combined features of brilliant red, star-shaped, single-type flowers; numerous, umbrella-shaped inflorescences, well above the foliage; medium sized, green, fan-shaped leaves with strong zonation; medium sized, rounded and well-branched plant habit; an beginning of flowering in mid season with continuous flowering.

1 Drawing Sheet

Genus and species of the plant claimed: *Pelargonium zonale* L'Héritier (hybrid).
Variety denomination: 'Grafire'.

BACKGROUND OF THE INVENTION

The present invention comprises a new and distinct cultivar of *geranium*, botanically known as *Pelargonium zonale,* and hereinafter referred to by the cultivar name 'Grafire'.

'Grafire' is a product of a planned breeding program which had the objective of creating new stellar-type *germanium* cultivars in various flower colors, in combination with early flowering, zoned foliage, and about medium sized, rounded and well-branched plant habit.

'Grafire' originated from a hybridization made by the inventor, Angelika Utecht, in a controlled breeding program in Hellscheid, Germany, in 1999. The female parent was an unpatented hybrid plant, no. 88-380-1, having small, red single-type flowers, medium green foliage with distinct zonation, and relatively compact plant habit. The male parent of 'Grafire' was the unpatented commercial variety 'Vectis Glitter', with single-type, white flowers with irregularly spread small red dots or fine stripes, large inflorescences, and vigorous growth habit.

'Grafire' was selected as one flowering plant within the progeny of the stated cross by Angelika Utecht in 2000 in a controlled environment in Fuerteventura, Canary Islands, Spain.

The first act of asexual reproduction of 'Grafire' was accomplished when vegetative cuttings were taken from the initial selection in the fall of 2000 in a controlled environment in Fuerteventura, Spain, by, or under the supervision of, Angelika Utecht.

Horticultural examination of plants grown from cuttings of the plant initiated in May of 2001, in Hillscheid, Germany, and continuing thereafter, has demonstrated that the combination of characteristics as herein disclosed for 'Grafire' are firmly fixed and are retained through successive generations of asexual reproduction.

BRIEF SUMMARY OF THE INVENTION

'Grafire' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Grafire' in combination distinguish this *geranium* as a new and distinct cultivar:

1. brillant red, single-type flowers;
2. medium sized, umbrella-shaped inflorescences, well above the foliage;
3. medium sized, fan-shaped leaves with strong zonation;

4. medium sized and well-branched plant habit; and 5. beginning of flowering in mid season.

Of the many commercial cultivars known to the present inventor, the most similar in comparison to 'Grafire' are the patented variety 'Fiwoscarl' (U.S. Plant Pat. No. 13,303) and the unpatented variety 'Red Flash', also known by breeder's ref. KLEP01002.

In comparison to 'Fiwoscarl', 'Grafire' has similar flower size and color, but roughly semi-circular leaf blades whereas the leaves of 'Fiwoscarl' are kidney-shaped. Further, the plant habit of 'Fiwoscarl' is generally taller and with a higher foliage canopy than 'Grafire'.

In comparison to 'Red Flash', with numerous small inflorescence, and compact plant habit, 'Grafire' has larger and flatter shaped umbels, foliage with less strong zonation, and taller, medium sized, plant habit.

BRIEF DESCRIPTION OF THE DRAWING

The accompanying photographic drawing shows typical flower and foliage characteristics of 'Grafire' with colors being as true as possible with an illustration of this type. The photographic drawing shows a side view perspective of a flowering potted plant of 'Grafire' with leaves, buds and inflorescences.

DETAILED BOTANICAL DESCRIPTION

The measurements were taken in Hillscheid, Germany, in mid May, 11 weeks after planting of rooted cuttings. The plants were growing in 14 cm pots, they had not been pinched.

In the following description, color references are made to The Royal Horticultural Society Color Chart. The color values were determined indoors from plants growing in a green-house in May 2003 in Hillscheid, Germany.

Parentage:
- *Male parent.*—'Vectis Glitter', unpatented commercial variety.
- *Female parent.*—Unpatented, hybrid plant no. 88-380-1.

Classification: *Pelargonium zonale* L'Héritier (hybrid).

Propagation: Vegetative cuttings.

Inflorescence:

Umbel:
- *Shape.*—Umbrella-shape.
- *Average diameter.*—83 mm.
- *Average depth.*—45 mm.
- *Number of flowers per umbel.*—20–25.

Peduncle:
- *Peduncle length.*—159 mm.
- *Peduncle diameter.*—3–4 mm.
- *Peduncle color.*—Light grey-red, RHS 179 B, lower part yellow-green, RHS 144 B.

Pedicel:
- *Pedicel length.*—25 mm in length, usually with a spur.
- *Pedicel diameter.*—1.5 to 2 mm.
- *Pedicel color.*—Most parts grey-red infused, RHS 180 B, near the base yellow-green, RHS 152 D.

Corolla:
- *Average diameter.*—40 mm.
- *Depth.*—6 mm.
- *Form.*—Single-type.
- *Shape.*—Star-shape, with the 2 upper petals narrower than the lower petals.
- *Number of petaloids.*—None.

Petals:
- *Number of petals.*—5.
- *Shape of petals.*—Upper petals narrow elliptical, lower petals rhomboid, with acute base and acuminate tips.
- *Size of petals.*—Upper petals: 22 mm long, 8 mm wide; lower petals: 20 mm long, 10 mm wide.
- *Margin of petals.*—Upper petals: lower and middle part entire, dentate near the tip; lower petals: slightly crenate towards the tip, basal part entire.
- *Color (general tonality from a distance of three meters).*—Red.
- *Color of upper petals.*—Red, RHS 44 A.
- *Markings of upper petals.*—No distinct markings.
- *Color of lower petals.*—Red, RHS 44 A.
- *Markings of lower petals.*—None.
- *Color of lower surface of petals.*—Red, RHS 41 A.

Sepals:
- *Color of sepals.*—Outer surface: yellow-green, RHS 144 B; inner surface: yellow-green, RHS 144 B.
- *Number of sepals.*—5.
- *Shape of sepals.*—Ensiform, acute tip, fused base, surface with very short pubescence, margin entire.
- *Size of sepals.*—9–10 mm long, 3 mm wide for the largest upper sepal, 2 mm in width for the other sepals.

Bud (just prior to petals unfolding):
- *Shape.*—Narrow, elliptical.
- *Color of sepals.*—Yellow-green, RHS 144 B.
- *Color of petals.*—Red, RHS 45 B.
- *Length.*—13–14 mm.
- *Width.*—6 mm.

Reproductive organs:

Androecium: 5 fertile anthers, moderate pollen, orange-red, RHS 30 A, filaments white, RHS 155 D, to light-pink, RHS 52 D.

Gynoecium: One pistil, whitish style, RHS 155 D to red-purple, RHS 65 D, stigma 5–6-lobed and pink, RHS 50 A, in color.

Fertility/seed set: No seed set observed.

Spring flowering response period: In Hillscheid, Germany, in 2003 plants had on average 0.8 flowers opened 9 weeks after planting of rooted cuttings.

Outdoor flower production: Continuously and rich flowering, the flower count in 2003 in Hillscheid, Germany, indicated about 20 inflorescences per plant in late summer.

Durability: Good stability of flower color, no fading, fair rain resistance.

Lastingness of the individual flower: About 7–8 days at 18° C., about 16 days for the umbel.

Fragrance: None.

Plant:

Foliage:
- *Shape.*—Roughly semi-circular to flabellate, apex rounded with distinct lobes, base truncate to obtuse.
- *Margin.*—Tips of lobes dentate, base entire.
- *Texture.*—Upper surface smooth, dull.
- *Size of leaf.*—87 mm wide, 50 mm long.
- *Color of upper surface.*—Green, approximately RHS 143 B.
- *Color of zonation.*—Strong, brown (greyed-orange), about RHS 166 A.
- *Color of lower surface.*—Green, RHS 143 B to 143 C.
- *Petioles.*—65–75 mm long, 2.0–2.5 mm diameter, light green in color, approximately RHS 143 B.

General appearance and form:

*Stem color.*—Mainly light green, RHS 143 C; in places slightly grayish-red infused, RHS 179 B.

*Internode length.*—15–25 mm.

*Branching pattern.*—12 branches.

*Size of plants.*—Height: 15.3 cm, Spread: 27.3 cm (11-week-old plants, as described, measured from the top of the soil (base of the main stem) to the surface of the foliage canopy, without inflorescences).

I claim:

1. A new and distinct cultivar of *geranium* plant named 'Grafire', as described and illustrated herein.

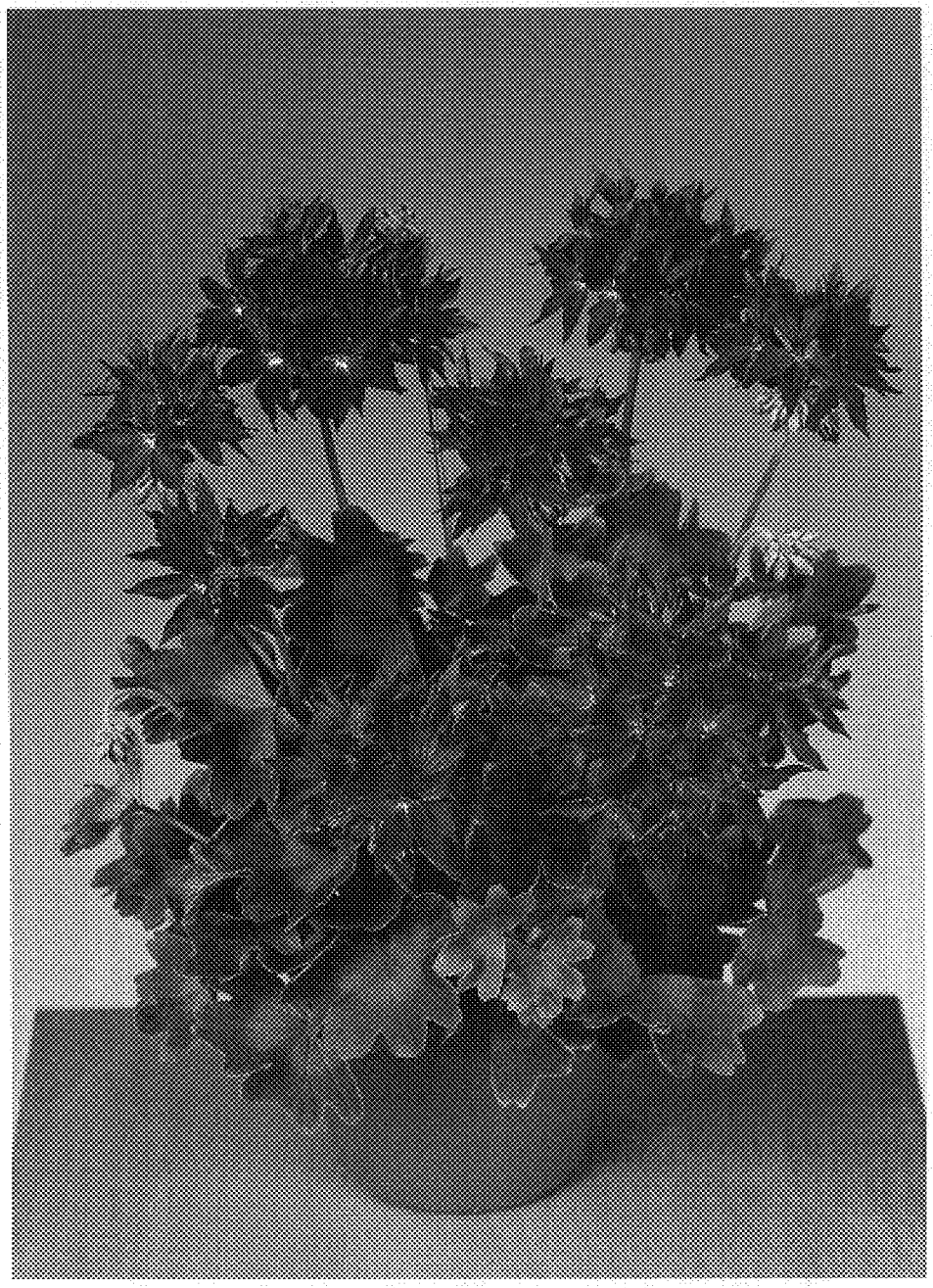

* * * * *